(12) United States Patent
Gambale et al.

(10) Patent No.: US 7,232,421 B1
(45) Date of Patent: Jun. 19, 2007

(54) AGENT DELIVERY SYSTEMS

(75) Inventors: Richard A. Gambale, Tyngsboro, MA (US); Chirag B. Shah, Nashua, NH (US); Michael F. Weiser, Groton, MA (US); Stephen J. Forcucci, Medford, MA (US); Sean Forde, Watertown, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/743,726

(22) PCT Filed: May 12, 2000

(86) PCT No.: PCT/US00/13119

§ 371 (c)(1),
(2), (4) Date: Apr. 12, 2001

(87) PCT Pub. No.: WO00/13119

PCT Pub. Date: May 12, 2000

(51) Int. Cl.
*A61M 31/00* (2006.01)
(52) U.S. Cl. .................................................. 604/57
(58) Field of Classification Search .................. 606/1, 606/108, 194, 198, 200; 623/1, 12; 604/57, 604/58, 59, 60, 62, 63, 64, 890.1, 891.1, 604/892.1
See application file for complete search history.

(56) References Cited

U.S. PATENT DOCUMENTS 2,761,446 A * 9/1956 Reed ............................ 604/61
2,969,963 A 1/1961 Brown
3,443,561 A * 5/1969 Reed .......................... 604/93.01
3,680,544 A 8/1972 Shinnick et al.

(Continued)

FOREIGN PATENT DOCUMENTS

DE 19703482 1/1997

(Continued)

OTHER PUBLICATIONS

A. Hassan Khazei et al., "Myocardial Canalization, A new Method of Myocardial Revascularization", *The Annals of Thoracic Surgery*, vol. 6, No. 2, pp. 163-171, Aug. 1968.

(Continued)

*Primary Examiner*—Manuel Mendez
(74) *Attorney, Agent, or Firm*—Kirkpatrick & Lockhart Preston Gates Ellis LLP

(57) ABSTRACT

The present invention provides a system for delivering a therapeutic agent into tissue in combination with an implant device (2). Preferably the therapeutic substance is contained within a pellet form (14) that is deliverable into the interior of the device (2) after it has been implanted. In a preferred embodiment the implant device (2) comprises a flexible coiled spring body, the coils (4) of which have the proper diameter and spacing to contain the pellet (14) within the interior of the device (2) to contact the therapeutic agent. In treatment of ischemic tissue such as that of the myocardium of the heart, the mechanical irritation of the tissue caused by the implanted device (2) can help to provide an angiogenic effect. Additionally, the cavity (18) provided by the interior of the device (2) permits blood to pool around the pellet (14) and mix with the therapeutic agent. Several delivery systems have provided for delivering the implant and pellet (14) sequentially or simultaneously.

11 Claims, 8 Drawing Sheets

U.S. PATENT DOCUMENTS

| | | |
|---|---|---|
| 3,991,750 A | 11/1976 | Vickery |
| 3,995,617 A | 12/1976 | Watkins et al. |
| 4,223,674 A * | 9/1980 | Fluent et al. ............... 128/217 |
| 4,237,884 A * | 12/1980 | Erickson et al. .............. 604/57 |
| 4,307,722 A | 12/1981 | Evans et al. |
| 4,326,522 A | 4/1982 | Guerrero et al. |
| 4,451,253 A | 5/1984 | Harman |
| 4,461,280 A | 7/1984 | Baumgartner |
| 4,479,796 A * | 10/1984 | Kallok .................... 604/93.01 |
| 4,503,569 A | 3/1985 | Dotter |
| 4,546,499 A | 10/1985 | Possis |
| 4,562,597 A | 1/1986 | Possis et al. |
| 4,580,568 A | 4/1986 | Gianturco |
| 4,582,181 A | 4/1986 | Samson |
| 4,641,653 A | 2/1987 | Rockey |
| 4,649,922 A | 3/1987 | Wiktor |
| 4,655,771 A | 4/1987 | Wallsten |
| 4,658,817 A | 4/1987 | Hardy et al. |
| 4,665,918 A | 5/1987 | Garza et al. |
| 4,681,110 A | 7/1987 | Wiktor |
| 4,700,692 A | 10/1987 | Baumgartner |
| 4,718,425 A | 1/1988 | Tamaka et al. |
| 4,731,054 A * | 3/1988 | Billeter et al. .......... 604/93.01 |
| 4,733,665 A | 3/1988 | Palmaz |
| 4,762,515 A * | 8/1988 | Grimm ........................ 604/61 |
| 4,768,507 A | 9/1988 | Fischell et al. |
| 4,774,949 A | 10/1988 | Fogarty |
| 4,785,815 A | 11/1988 | Cohen |
| 4,791,939 A | 12/1988 | Maillard |
| 4,813,925 A | 3/1989 | Anderson, Jr. et al. |
| 4,820,267 A * | 4/1989 | Harman ....................... 604/60 |
| 4,852,580 A | 8/1989 | Wood |
| 4,861,330 A | 8/1989 | Voss |
| 4,889,137 A | 12/1989 | Kolobow |
| 4,904,264 A | 2/1990 | Scheunemann |
| 4,909,250 A | 3/1990 | Smith |
| 4,917,666 A | 4/1990 | Solar et al. |
| 4,920,980 A | 5/1990 | Jackowski |
| 4,950,227 A | 8/1990 | Savin et al. |
| 4,995,857 A | 2/1991 | Arnold |
| 4,997,431 A | 3/1991 | Isner et al. |
| 5,040,543 A | 8/1991 | Badera et al. |
| 5,042,486 A | 8/1991 | Pfeiler et al. |
| 5,047,028 A | 9/1991 | Qian |
| 5,049,138 A | 9/1991 | Chevalier et al. |
| 5,056,517 A | 10/1991 | Fenici |
| 5,062,829 A * | 11/1991 | Pryor et al. .................. 604/57 |
| 5,087,243 A | 2/1992 | Avitall |
| 5,098,374 A | 3/1992 | Othel-Jacobsen et al. |
| 5,114,414 A | 5/1992 | Buchbinder |
| 5,158,548 A | 10/1992 | Lau et al. |
| 5,167,614 A | 12/1992 | Tessmann et al. |
| 5,172,699 A | 12/1992 | Svenson |
| 5,176,626 A | 1/1993 | Soehendra |
| 5,180,366 A | 1/1993 | Woods |
| 5,190,058 A | 3/1993 | Jones et al. |
| 5,256,146 A | 10/1993 | Ensminger et al. |
| 5,266,073 A | 11/1993 | Wall |
| 5,269,326 A | 12/1993 | Verrier |
| 5,287,861 A | 2/1994 | Wilk |
| 5,290,295 A | 3/1994 | Querals et al. |
| 5,312,456 A | 5/1994 | Reed et al. |
| 5,324,325 A | 6/1994 | Moaddeb |
| 5,328,470 A | 7/1994 | Nabel et al. |
| 5,366,493 A | 11/1994 | Scheiner et al. |
| 5,372,600 A | 12/1994 | Beyar et al. |
| 5,376,071 A | 12/1994 | Henderson |
| 5,380,316 A | 1/1995 | Aita et al. |
| 5,386,828 A | 2/1995 | Owens et al. |
| 5,389,096 A | 2/1995 | Aita et al. |
| 5,391,199 A | 2/1995 | Ben-Haim |
| 5,405,376 A | 4/1995 | Mulier et al. |
| 5,409,004 A | 4/1995 | Sloan |
| 5,409,019 A | 4/1995 | Wilk |
| 5,423,885 A | 6/1995 | Williams |
| 5,425,757 A | 6/1995 | Tiefenbrun et al. |
| 5,429,144 A | 7/1995 | Wilk |
| 5,441,516 A | 8/1995 | Wang et al. |
| 5,452,733 A | 9/1995 | Sterman et al. |
| 5,453,090 A | 9/1995 | Martinez et al. |
| 5,458,615 A | 10/1995 | Klemm |
| 5,464,404 A | 11/1995 | Abela et al. |
| 5,464,650 A | 11/1995 | Berg et al. |
| 5,466,242 A | 11/1995 | Mori |
| 5,476,505 A | 12/1995 | Limon |
| 5,480,422 A | 1/1996 | Ben-Haim |
| 5,487,739 A | 1/1996 | Aebischer et al. |
| 5,501,664 A | 3/1996 | Kaldany |
| 5,514,176 A | 5/1996 | Bosley, Jr. et al. |
| 5,551,427 A | 9/1996 | Altman |
| 5,551,954 A | 9/1996 | Buscemi et al. |
| 5,558,091 A | 9/1996 | Acker et al. |
| 5,562,613 A | 10/1996 | Kaldany |
| 5,562,619 A | 10/1996 | Mirarchi et al. |
| 5,562,922 A | 10/1996 | Lambert |
| 5,569,272 A | 10/1996 | Reed et al. |
| 5,571,168 A | 11/1996 | Toro |
| 5,593,412 A | 1/1997 | Martinez et al. |
| 5,593,434 A | 1/1997 | Williams |
| 5,602,301 A | 2/1997 | Field |
| 5,614,206 A | 3/1997 | Randolf et al. |
| 5,618,563 A | 4/1997 | Berde et al. |
| 5,629,008 A | 5/1997 | Lee |
| 5,635,215 A | 6/1997 | Boschetti et al. |
| 5,643,308 A | 7/1997 | Markman |
| 5,653,756 A | 8/1997 | Clarke et al. |
| 5,655,548 A | 8/1997 | Nelson |
| 5,656,029 A | 8/1997 | Imran et al. |
| 5,662,124 A | 9/1997 | Wilk |
| 5,676,850 A | 10/1997 | Reed et al. |
| 5,682,906 A | 11/1997 | Sterman et al. |
| 5,690,643 A | 11/1997 | Wijay |
| 5,735,897 A | 4/1998 | Buirge |
| 5,741,330 A | 4/1998 | Brauker et al. |
| 5,744,515 A | 4/1998 | Clapper |
| 5,755,682 A | 5/1998 | Knudson et al. |
| 5,756,127 A | 5/1998 | Grisoni et al. |
| 5,762,600 A | 6/1998 | Bruchman et al. |
| 5,769,843 A | 6/1998 | Abela et al. |
| 5,782,823 A | 7/1998 | Mueller |
| 5,785,702 A | 7/1998 | Murphy et al. |
| 5,792,453 A | 8/1998 | Hammond et al. |
| 5,797,870 A | 8/1998 | March et al. |
| 5,807,384 A | 9/1998 | Mueller |
| 5,810,836 A | 9/1998 | Hussein |
| 5,817,101 A | 10/1998 | Fiedler |
| 5,824,049 A | 10/1998 | Ragheb et al. |
| 5,824,071 A | 10/1998 | Nelson et al. |
| 5,827,304 A | 10/1998 | Hart |
| 5,830,502 A | 11/1998 | Dong et al. |
| 5,833,608 A | 11/1998 | Acker |
| 5,840,059 A | 11/1998 | March et al. |
| 5,851,217 A | 12/1998 | Wolff et al. |
| 5,861,032 A | 1/1999 | Subramaniam |
| 5,868,699 A | 2/1999 | Woodruff et al. |
| 5,879,383 A | 3/1999 | Bruchman et al. |
| 5,891,108 A * | 4/1999 | Leone et al. ................. 604/264 |
| 5,893,869 A | 4/1999 | Barnhart et al. |
| 5,899,915 A | 5/1999 | Saadat |
| 5,968,052 A | 10/1999 | Sullivan, III et al. |
| 5,971,993 A | 10/1999 | Hussein |
| 5,980,514 A | 11/1999 | Kupiecki et al. |
| 5,980,548 A | 11/1999 | Evans et al. |
| 5,980,566 A * | 11/1999 | Alt et al. ....................... 623/1 |

| | | | |
|---|---|---|---|
| 5,984,890 A * | 11/1999 | Gast et al. ..................... 604/60 |
| 6,019,779 A * | 2/2000 | Thorud et al. ............... 606/198 |
| 6,036,666 A * | 3/2000 | Peiler et al. .................. 604/11 |
| 6,045,565 A | 4/2000 | Ellis et al. |
| 6,051,001 A | 4/2000 | Borghi |
| 6,053,924 A | 4/2000 | Hussein |
| 6,086,582 A | 7/2000 | Altman et al. |
| 6,192,271 B1 * | 2/2001 | Hayman ...................... 604/21 |
| 6,197,324 B1 | 3/2001 | Crittenden |
| 6,206,915 B1 * | 3/2001 | Fagan et al. ................ 623/1.42 |
| 6,248,112 B1 | 6/2001 | Gambale et al. |
| 6,251,079 B1 | 6/2001 | Gambale et al. |
| 6,251,418 B1 | 6/2001 | Ahern et al. |
| 6,263,880 B1 | 7/2001 | Parker et al. |
| 6,277,082 B1 | 8/2001 | Gambale |
| 6,432,126 B1 | 8/2002 | Gambale et al. |
| 6,447,522 B2 | 9/2002 | Gambale et al. |
| 6,458,092 B1 | 10/2002 | Gambale et al. |

FOREIGN PATENT DOCUMENTS

| | | |
|---|---|---|
| DE | 29619029 | 4/1997 |
| EP | 0 132 387 | 1/1985 |
| EP | 0 363 661 | 4/1990 |
| EP | 0 515 867 A2 | 12/1992 |
| EP | 0 584 959 A2 | 7/1993 |
| EP | 0 490 459 A1 | 10/1994 |
| EP | 0 714 640 A1 | 6/1996 |
| EP | 0 717 969 A2 | 6/1996 |
| EP | 0 732 089 A2 | 9/1996 |
| EP | 0 812 574 A2 | 12/1997 |
| EP | 0 830 873 A2 | 3/1998 |
| EP | 0 853 921 A2 | 7/1998 |
| EP | 0 953 320 A2 | 11/1999 |
| EP | 1 078 610 A2 | 2/2001 |
| FR | 1514319 | 1/1967 |
| FR | 2725615 | 10/1994 |
| FR | 1278965 | 1/1996 |
| RU | 2026640 C1 | 1/1995 |
| RU | 2063179 C1 | 7/1996 |
| WO | WO 89/01798 | 3/1989 |
| WO | WO 90/06723 | 6/1990 |
| WO | WO 91/15254 | 10/1991 |
| WO | WO 94/05265 | 3/1994 |
| WO | WO 94/.27612 | 12/1994 |
| WO | WO 96/13303 | 10/1995 |
| WO | WO 95/33511 | 12/1995 |
| WO | WO 96/39830 | 5/1996 |
| WO | WO 96/40368 | 6/1996 |
| WO | WO 96/20698 | 7/1996 |
| WO | WO 97/16169 | 10/1996 |
| WO | WO 97/42910 | 7/1997 |
| WO | WO 97/32551 | 9/1997 |
| WO | WO 97/38730 | 10/1997 |
| WO | WO 97/44071 | 11/1997 |
| WO | WO 97/45105 | 12/1997 |
| WO | WO 97/47253 | 12/1997 |
| WO | WO 98/05307 | 2/1998 |
| WO | WO 98/08456 | 3/1998 |
| WO | WO 98/16644 | 4/1998 |
| WO | WO 98/23228 | 6/1998 |
| WO | WO 98/25533 | 6/1998 |
| WO | WO 98/29148 | 7/1998 |
| WO | WO 98/32859 | 7/1998 |
| WO | WO 98/46115 | 10/1998 |
| WO | WO 99/21510 | 5/1999 |
| WO | WO 99/38459 | 8/1999 |
| WO | WO 99/53863 | 10/1999 |

OTHER PUBLICATIONS

Alfred Goldman et al., "Experimental Methods for Producing a Collateral Circulation to the Heart Directly from the Left Ventricle", *Journal of Thoracic Surgery*, vol. 31, No. 3, pp. 364-374, Mar. 1956.

A. Sachinopoulou et al., "Invited Review Transmyocardial Revascularization", *Lasers in Medical Science*, 1995, vol. 10, pp. 83-91, Sep. 1995.

B. Schumacher et al., Induction of Neoangiogenesis in Ischemic Myocardium by Human Growth Factors, First Clinical Results of a New Treatment of Coronary Heart Disease, Clinical Investigation and Reports, pp. 645-650, Dec. 1997.

Charles T. Dotter, Transluminally-placed Coilspring Endarterial Tube Grafts: Long-term Patency in Canine Popliteal Artery, Investigative Radiology, pp. 329-332, Sep.-Oct. 1969.

C. Massimo, et al., Myocardial Revascularization By a New Method of Carrying Blood Directly from the Left Ventricular Cavity into the Coronary Circulation, Journals of Thoracic Surgery, vol. 34, No. 2, pp. 257-264, Aug. 1957.

Garrett Lee et al., Feasibility of Intravascular Laser Irradiation for in vivo Visualization and therapy of Cardiocirculatory Diseases, American Heart Journal., vol. 103 No. 6, pp. 1076-1077.

Garrett Lee et al., Laser-Dissolution of Coronary Atherosclerotic Obstruction, American Heart Journal, vol. 102, No. 6, part 1, pp. 1074-1075, Dec. 1981.

George S. Abela et al., Use of Laser Radiation to Recanalize Totally Obstructed Coronary Arteries (Abstract), Journal American College Cardiology, 1983:1(2):691.

George S. Abela et al., Laser Revascularization: What Are Its Prospects?, Journal of Cardiovascular Medicine, pp. 977-984, Sep. 1983.

Isam N. Anabtawi et al., Experimental Evaluation of Myocardial Tunnelization as a Method of Myocardial Revascularization, Journal of Thoracic and Cardiovascular Surgery, vol. 58, No. 5, pp. 638-646, Nov. 1969.

John E. Hershey et al., Transmyocardial Puncture Revascularization, Geriatrics, pp. 101-108, Mar. 1969.

Ladislav Kuzela et al. Experimental Evaluation of Direct Transventricular Revascularization, Journal of Thoracic Cardiovascular Surgery, vol. 57, No. 6, pp. 770-773, Jun. 1969.

Mahmood Mirhoseini et al., Myocardial Revascularization by Laser: A Clinical Report; Lasers in Surgery and Medicine 3:241-245 (1983).

Mahmood Mirhoseini et al. Revascularization of the Heart by Laser; Journal of Microsurgery, pp. 253-260, Jun. 1981.

Mahmood Mirhoseini et al., Transventricular Revascularization by Laser, Lasers in Surgery and Medicine, vol. 2, pp. 1987-198, 1982.

Mahmood Mirhoseini et al., Clinical Report: Laser Myocardial Revascularization, Lasers in Surgery and Medicine vol. 6, pp. 459-461, 1986.

Mahmood Mirhoseini et al., New Concepts in Revascularization of the Myocardium, The Annals of Thoracic Surgery, vol. 45, No. 4, pp. 415-420, Apr. 1988.

P. Walter et al., Treatment of Acute Myocardial Infarction by Transmural Blood Supply from the Ventricular Cavity, Department of Surgery and Department of Radiology of the Hanover Medical School, Hanover, pp. 130-138, (1971).

Peter Whittaker, et al., Transmural Channels Can Protect Ischemic Tissue, Assessment of Long-term Myocardial Response to Laser and Needle-Made Channels, Circulation, vol. 93, No. 1, pp. 143-152, Jan. 1996.

P.K. Sen. et al., Further Studies in Multiple Transmyocardial Acupuncture as a Method of Myocardial Revascularization, Surgery, vol. 64, No. 5, pp. 861-870, No. 1968.

P.K. Sen, et al, Transmyocardial Acupuncture, A New Approach to Myocardial Revascularization; Journal of Thoracic and Cardiovascular Surgery, vol. 50, No. 2, pp. 181-189, Aug. 1965.

R.I. Hardy et al., Regional Myocardial Blood Flow and Cardiac Mechanics in Dog Hearts with $CO_2$ Laser-Induced Intramyocardial Revascularization, Basic Research Cardiology, 85:179-197 (1990).

Roque Pifarre et al., Myocardial Revascularization by Transmyocardial Acupuncture: A Physiologic Impossibility; Journal of Thoracic and Cardiovascular Surgery; vol. 58, No. 3, pp. 424-429, Sep. 1969.

Valluvan Jevanandam et al., Myocardial Revascularization of Laser-Induced Channels, Surgical Forum vol. VL, American College of Surgeons 76th Clinical Congress, vol. 4, pp. 225-227, Oct. 1990.

Neil B. Ingels, et al., Measurement of Midwall Myocardial Dynamics in Intact Man by Radiography of Surgically Implanted Markers, Circulation, vol. 52, pp. 859-867 (Nov. 1975).

Dr. Joachim Burhenne, "Less Invasive Medicine: Historical Perspectives", *Boston Scientific Home Page, Corporate Information/Special Report*, pp. 1-11.

Mark Freed, M.D. et al., "The New Manual of Interventional Cardiology", *Physicians' Press, Division of Cardiology, William Beaumont Hospital*, Royal Oak, Michigan, pp. 645-660 (1996).

A. Michael Lincoff, M.D. et al. "Local Drug Delivery for the Prevention of Restenosis Fact, Fancy and Future", *Cleveland Clinic Foundation, The Department of Cardiology*, Cleveland, Ohio, vol. 90, No. 4, pp. 2070-2084 (1994).

Reimer Reissen, M.D. et al., "Prospects for Site-Specific Delivery of Pharmacologic and Molecular Therapies", *JAAC*, vol. 23, No. 5.

Bruce F. Waller, M.D., "Anatomy, Histology, and Pathology of the Major Epicardial Coronary Arteries Relevant to Echocardiographic Imaging Techniques", *J. A. Soc. Echo.*, vol. 2, pp. 232-252 (1989).

Robert L. Wilensky et al., "Methods and Devices for Local Drug Delivery in Coronary and Peripheral Arteries", *TCM*, vol. 3, No. 5 (1993).

M. A. Martinelli, et al., "Intraluminal Ultrasound Guidance of Transverse Laser Coronary Arthrectomy", *Optical Fibers in Medicine*, vol. 1201, pp. 68-78, (1990).

U.S. Appl. No. 09/073,118, filed May 5, 1998, Gambale.
U.S. Appl. No. 09/159,834, filed Sep. 24, 1998, Cafferata.
U.S. Appl. No. 09/162,547, filed Sep. 29, 1998, Gambale.
U.S. Appl. No. 09/211,332, filed Dec. 15, 1998, Gambale et al.
U.S. Appl. No. 09/299,795, filed Apr. 26, 1999, Ahern.
U.S. Appl. No. 09/328,808, filed Jun. 9, 1999, Ahern.
U.S. Appl. No. 09/368,119, filed Aug. 4, 1999, Tedeschi et al.
U.S. Appl. No. 09/743,695, filed Apr. 12, 2001, Weiser et al.
U.S. Appl. No. 09/774,319, filed Jan. 31, 2001, Gambale et al.
U.S. Appl. No. 09/774,320, filed Jan. 31, 2001, Gambale et al.
U.S. Appl. No. 09/888,757, filed Jun. 25, 2001, Ahern et al.
U.S. Appl. No. 09/990,644, filed Nov. 21, 2001, Gambale et al.
U.S. Appl. No. 10/048,205, filed May 2, 2002, Gambale.
U.S. Appl. No. 10/048,694, filed Jun. 10, 2002, Gambale et al.

* cited by examiner

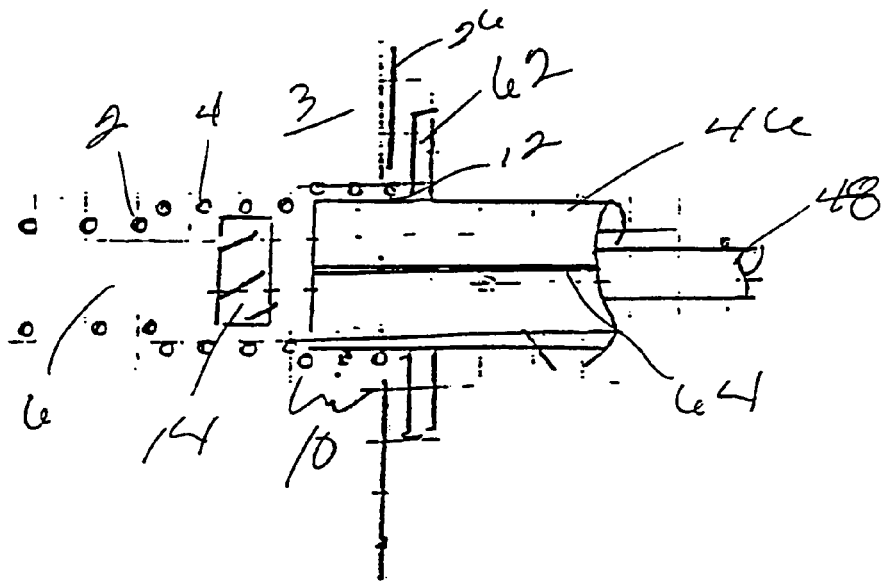
FIG. 7
FIG. 8A.   FIG. 8B
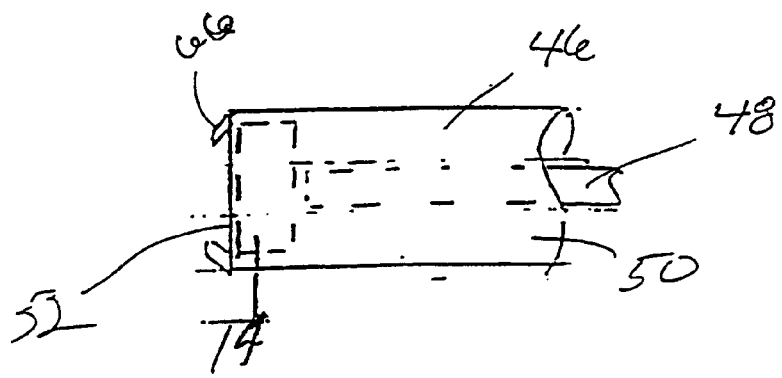
FIG. 9

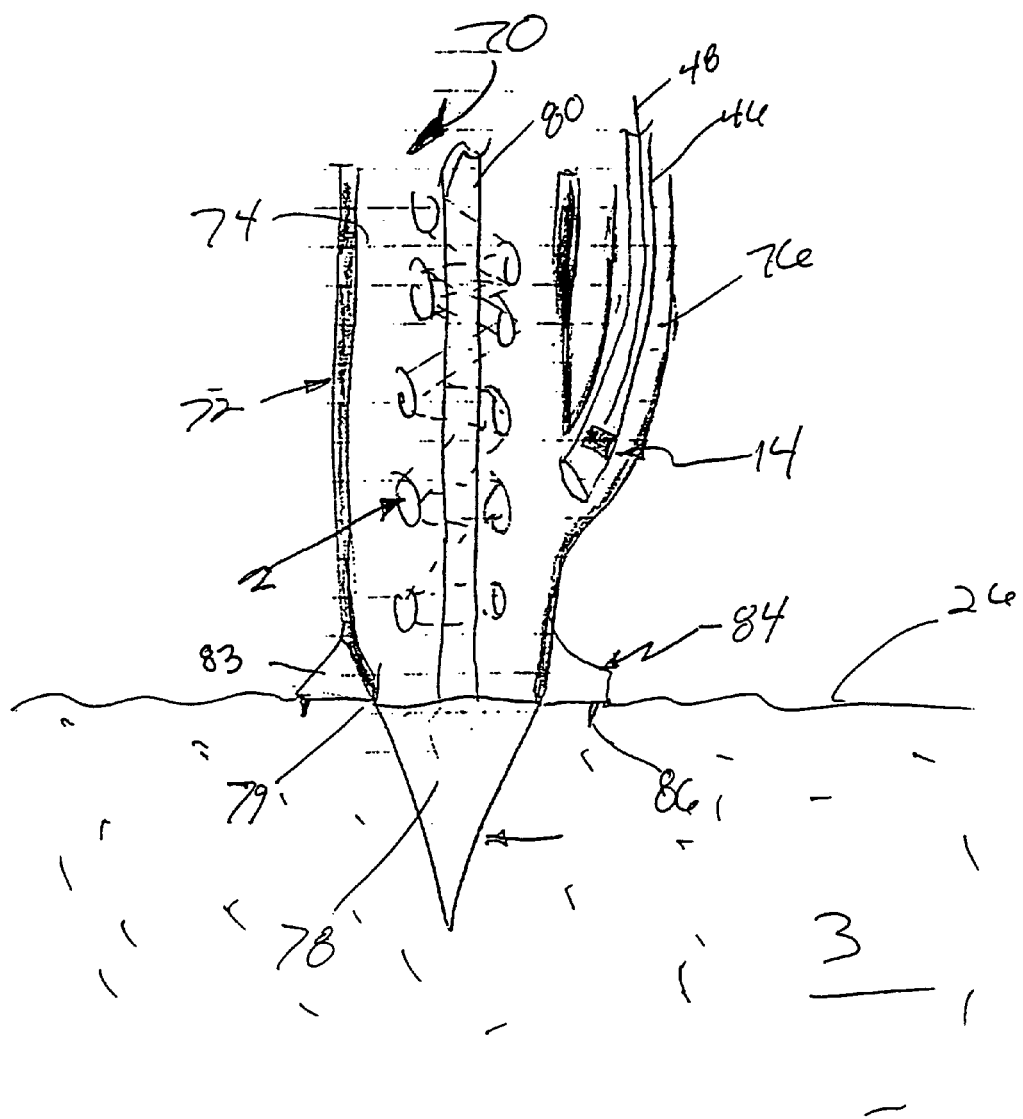

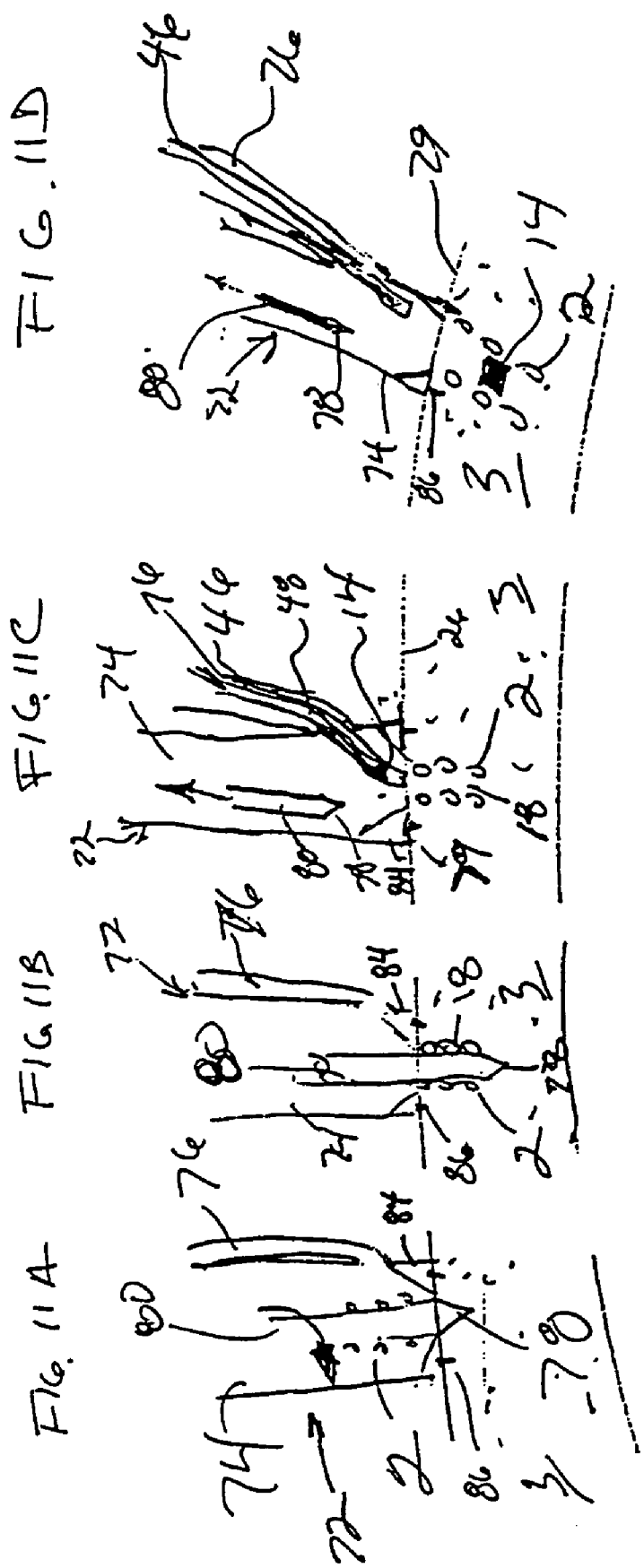

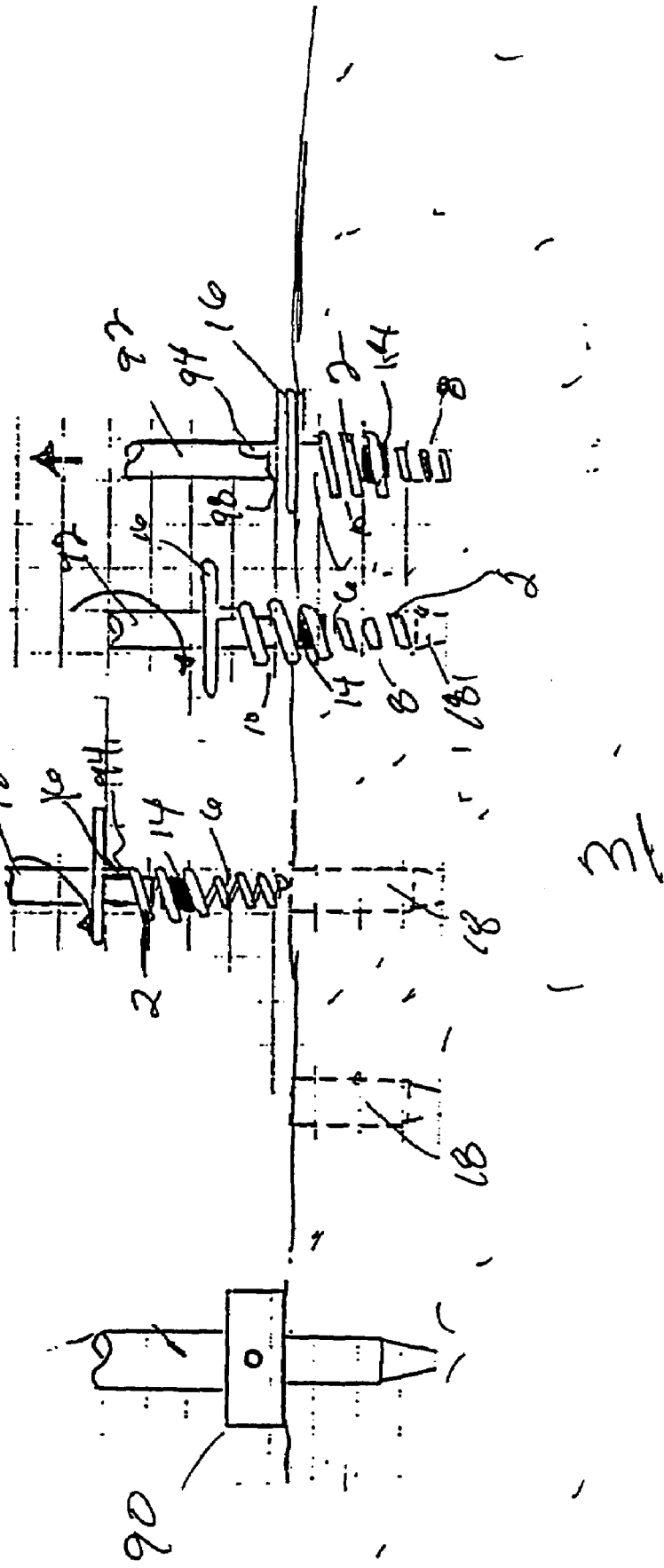

AGENT DELIVERY SYSTEMS

FIELD OF THE INVENTION

The present invention relates to delivery of a therapeutic agent into tissue in combination with an implant device. Specifically, the agent is contained in a pellet form capturable within the implant device to provide the therapeutic advantages provided by both in a single treatment.

BACKGROUND OF THE INVENTION

Tissue becomes ischemic when it is deprived of adequate blood flow. Ischemia causes pain in the area of the affected tissue and, in the case of muscle tissue, can interrupt muscular function. Left untreated, ischemic tissue can become infarcted and permanently non-functioning. Ischemia can be caused by a blockage in the vascular system that prohibits oxygenated blood from reaching the affected tissue area. However, ischemic tissue can be revived to function normally despite the deprivation of oxygenated blood because ischemic tissue can remain in a hibernating state, preserving its viability for some time. Restoring blood flow to the ischemic region serves to revive the ischemic tissue. Although ischemia can occur in various regions of the body, often myocardial tissue of the heart is affected by ischemia. Frequently, the myocardium is deprived of oxygenated blood flow due to coronary artery disease and occlusion of the coronary artery, which normally provides blood to the myocardium. The ischemic tissue causes pain to the individual affected.

Treatment of myocardial ischemia has been addressed by several techniques designed to restore blood supply to the affected region. A conventional approach to treatment of ischemia has been to administer anticoagulants with the objective of increasing blood flow by preventing formation of thrombus in the ischemic region.

Another conventional method of increasing blood flow to ischemic tissue of the myocardium is coronary artery bypass grafting (CABG). One type of CABG involves grafting a venous segment between the aorta and the coronary artery to bypass the occluded portion of the artery. Once blood flow is redirected to the portion of the coronary artery beyond the occlusion, the supply of oxygenated blood is restored to the area of ischemic tissue.

Early researchers, more than thirty years ago, reported promising results for revascularizing the myocardium by piercing the muscle to create multiple channels for blood flow. Sen, P. K. et al., "Transmyocardial Acupuncture—A New Approach to Myocardial Revascularization", *Journal of Thoracic and Cardiovascular Surgery*, Vol. 50, No. 2, August 1965, pp. 181–189. Although researchers have reported varying degrees of success with various methods of piercing the myocardium to restore blood flow to the muscle (which has become known generally as transmyocardial revascularization or TMR), many have faced common problems such as closure of the created channels. Various techniques of perforating the muscle tissue to avoid closure have been reported by researchers. These techniques include piercing with a solid sharp tip wire, or coring with a hypodermic tube. Reportedly, many of these methods produced trauma and tearing of the tissue that ultimately led to closure of the channel.

An alternative method of creating channels that potentially avoids the problem of closure involves the use of laser technology. Researchers have reported success in maintaining patent channels in the myocardium by forming the channels with the heat energy of a laser. Mirhoseini, M. et al., "Revascularization of the Heart by Laser", *Journal of Microsurgery*, Vol. 2, No. 4, June 1981, pp. 253–260. The laser was said to form channels in the tissue that were clean and made without tearing and trauma, suggesting that scarring does not occur and the channels are less likely to experience the closure that results from healing. U.S. Pat. No. 5,769,843 (Abela et al.) discloses creating laser-made TMR channels utilizing a catheter based system. Abela also discloses a magnetic navigation system to guide the catheter to the desired position within the heart. Aita U.S. Pat. Nos. 5,380,316 and 5,389,096 disclose another approach to a catheter based system for TMR.

Although there has been some published recognition of the desirability of performing TMR in a non-laser catheterization procedure, there does not appear to be evidence that such procedures have been put into practice. U.S. Pat. No. 5,429,144 (Wilk) discloses inserting an expandable implant within a preformed channel created within the myocardium for the purposes of creating blood flow into the tissue from the left ventricle.

Performing TMR by placing stents in the myocardium also is disclosed in U.S. Pat. No. 5,810,836 (Hussein et al.). The Hussein patent discloses several stent embodiments that are delivered through the epicardium of the heart, into the myocardium and positioned to be open to the left ventricle. The stents are intended to maintain an open channel in the myocardium through which blood enters from the ventricle and perfuses into the myocardium.

Angiogenesis, the growth of new blood vessels in tissue, has been the subject of increased study in recent years. Such blood vessel growth to provide new supplies of oxygenated blood to a region of tissue has the potential to remedy a variety of tissue and muscular ailments, particularly ischemia. Primarily, study has focused on perfecting angiogenic factors such as human growth factors produced from genetic engineering techniques. It has been reported that injection of such a growth factor into myocardial tissue initiates angiogenesis at that site, which is exhibited by a new dense capillary network within the tissue. Schumacher et al., "Induction of Neo-Angiogenesis in Ischemic Myocardium by Human Growth Factors", *Circulation,* 1998; 97:645–650.

SUMMARY OF THE INVENTION

The present invention provides a system for delivering an agent in combination with an implantable device to maximize a therapeutic benefit offered by each. Preferably the therapeutic agent is contained within a solid form such as a pellet or gel to facilitate its handling and to regulate its rate of dissipation into the tissue after delivery. The implant device is specially configured to receive and retain the pellet but permit blood to interact with the pellet so that the agent can be released to the blood in and around the device and the surrounding tissue. A delivery system comprises an implant delivery device having an obturator capable of piercing the tissue and a pellet delivery device to place a pellet into the interior of the implant after it has been implanted. Alternatively, the implant delivery device and the pellet delivery device may be contained in one apparatus to facilitate delivery of the pellet into the embedded implant. Alternatively, a system is disclosed for delivering the implant and pellet simultaneously.

The present invention is useful for treating tissue in any area of the body, especially ischemic tissue experiencing reduced blood flow. The present devices and methods are especially useful for treatment of ischemia of the myocardium. In treatment of the myocardium, the present implant device and pellet combination may be delivered percutaneously through a catheter based system into the endocardium of the heart, transthorasically or surgically through the epicardium of the heart.

With specific agents and a particular configuration of the implant device, revascularization by angiogenisis and vessel recruitment can be encouraged in the ischemic tissue by use of the present invention. A wide range of therapeutic agents conducive to revascularization can be introduced via the pellet including: growth factors; gene therapies or other natural or engineered substances formable in the pellet. The pellet formation is well known in the medical field and typically comprises an inert powder pressed together to form a tablet or pill-like article.

The implant device also provides therapeutic benefit to the subject tissue in several ways. First the structure of the implant device provides an interior cavity within the tissue which permits blood to pool, mix with the agents of the pellet and coagulate. The coagulation occurs in and around the device as part of the coagulation cascade, that will eventually lead to new vessel formation and recruitment. Additionally, the presence of a device in the moving tissue of a muscle such as the myocardium, creates an irritation or injury to the surrounding tissue which further promotes an injury response and the coagulation cascade that leads to new vessel growth. Additionally the implant causes a foreign body response, which causes inflammation attracting macrophages, which cause secretion of growth factors. Suitable implant devices are should be flexible, define an interior, be anchorable within tissue and permit fluid such as blood to transfer between the surrounding tissue and the interior of the device. Examples of tissue implant devices are disclosed in pending U.S. patent application Ser. Nos. 09/164,163, 09/164,173, 09/211,332 and 09/299,795, all of which are herein incorporated by reference. Delivery of therapeutic agents in a pellet form are discussed in pending U.S. application Ser. Nos. 08/993,586 and 09/116,313 and 09/159,834, all of which are herein incorporated by reference.

It is an object of the present invention to provide an agent delivery system that permits the delivery of an agent in combination with an implant device into tissue.

It is another object of the present invention to provide an implant device configured to retain a pellet containing a therapeutic substance while it is implanted in tissue.

It is another object of the invention to provide a delivery method for sequentially delivering the implant device and a pellet containing a therapeutic substance that is relatively simple and effective.

It is another object of the present invention to provide a method for delivering an implant device and pellet containing a therapeutic agent that utilizes a simplified delivery device.

It is yet another object of the present invention to provide a system and method for simultaneously delivering a pellet containing an agent within the interior of an implant device into tissue.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 7. is a partial sectional side view of a pellet and implant delivery system utilizing a depth monitor;

FIG. 8A. is an end view of a pellet delivery tube in its expanded condition;

FIG. 8B. is an end view of a pellet delivery tube in its relaxed position;

FIG. 9. is a side view of an alternate embodiment of the pellet delivery tube;

FIG. 10. is a partial sectional side view of an implant and pellet delivery system;

FIG. 11A. is a partial sectional side view of the delivery system of FIG. 10 introducing an implant into tissue;

FIG. 11B. is a partial sectional side view of the delivery system of FIG. 10 after implanting the device into tissue;

FIG. 11C. is a partial sectional side view of the delivery system of FIG. 10 delivering a pellet into the implanted device;

FIG. 11D. is a partial sectional side view of the delivery system of FIG. 10 after the pellet has been delivered into the implanted device;

FIG. 12A. is a side view of an obturator creating a channel according to an alternative delivery method;

FIG. 12B. is a side view of a created channel formed according to an alternative delivery method;

FIG. 12C. is a side view of an implant device and pellet being delivered into a channel by an insertion device according to an alternative delivery method;

FIG. 12D. is a side view of the insertion device rotating the implant device to insert it into the tissue according to an alternative delivery method;

FIG. 12E. is a side view of the insertion device being withdrawn from an implanted device and a pellet according to an alternative delivery method.

DESCRIPTION OF THE ILLUSTRATIVE EMBODIMENTS

Figure 1:
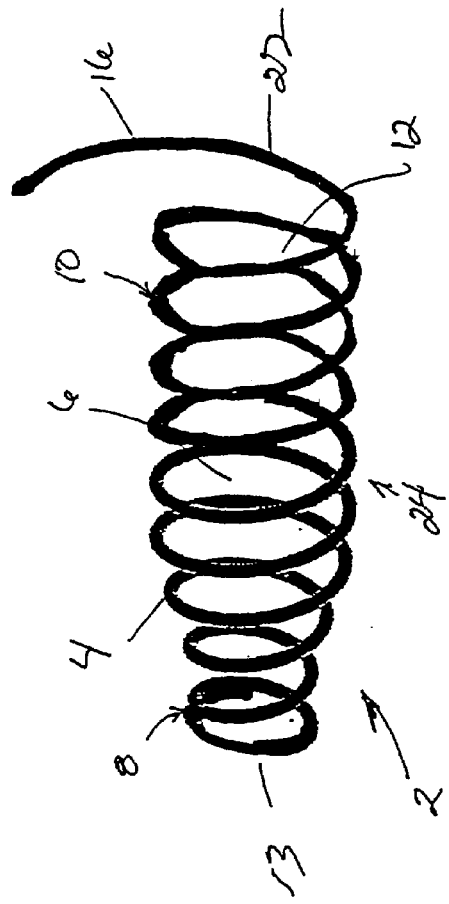
FIG. 1. is a side view of an implant device configured to accept a pellet.

FIG. 1 shows a side view of an implant device 2 of the present invention. In a preferred embodiment the implant device 2 comprises a flexible helical coil having a plurality of individual coils 4 that define an interior 6. The device preferably has a distal region 8 and proximal region 10. The coils at the distal region 8 define a diameter that is smaller than that defined by the coils of proximal region 10 so that a agent carrying pellet may be inserted through proximal opening 12 into the proximal region 10. The coils 4 of the distal region 8 are sized smaller than the pellet so that the pellet cannot enter the distal region. In the present application, proximal is understood to mean the direction leading external to the patient and distal is understood to mean any direction leading internally to the patient.

Figure 2:
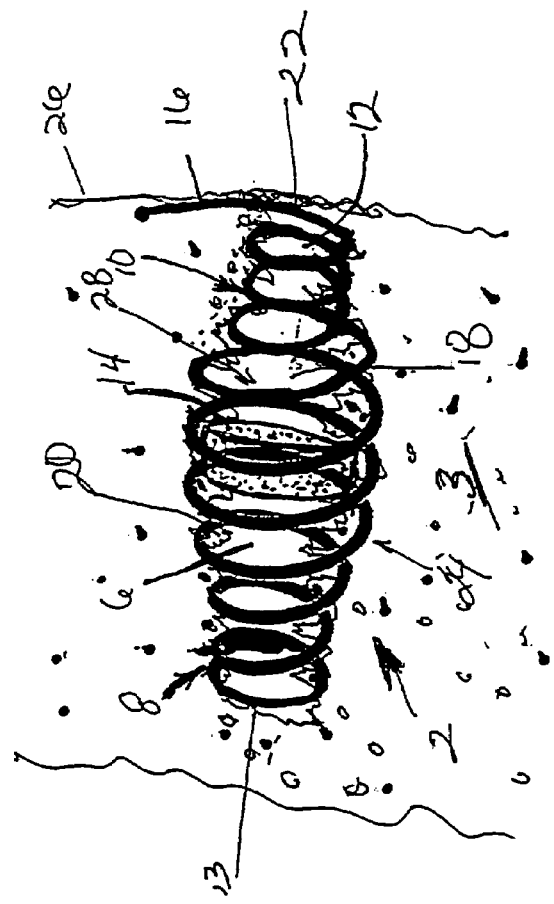
FIG. 2. is a side view of an implant device containing a pellet.

FIG. 2 shows the implant device 2 implanted in tissue 3 and having captured with its interior 6 a pellet 14. The implant device maintains a cavity 18 within the tissue defined by the interior 6 of the device where the pellet may reside and blood may pool and mix with agents contained in the pellet 14. After the device is implanted in tissue, by steps which will be described in detail below, a tail 16 joined to the proximal end 22 of the device 2 serves to prevent the device from migrating out of the tissue. The tail may comprise a variety of configurations but should extend to have a profile that is greater than the diameter of the coils along the body 24 of the device. The tail projects into the tissue and is submerged beneath the surface 26 of the tissue 3 to prevent axial migration as well as rotation of the device, which could permit the device to move from the tissue location. The pellet is maintained in position within the interior 6 of the device 2 by reducing the diameter of the coils 4 of the proximal portion 10 of the device after the pellet has been inserted. As mentioned above, the coils of the distal portion 8 are pre-formed to have a diameter that is smaller than the lateral extent of the pellet to prevent distal migration out of the device. The proximal portion coils 10 may be reduced in diameter by crimping by sterilized forceps after the implant device and pellet are delivered to the tissue. The reduced diameter coils of the proximal portion 10 and a distal portion 8 of the device leave a capturing portion 28 at the center of the device where the pellet will reside. The pellet may move slightly within this capturing portion 28 but will not migrate from either the proximal end 12 or distal end 13 of the device. In treating the myocardium of the heart a preferred device length is on the order of approximately 7 mm–8 mm. The device may be made from any implantable material such as surgical grades of stainless steel or a nickel titanium alloy.

Additionally, it is important to note that the pellet will be helped to be maintained in position within the device and within the capturing portion 28 by herniation points 20 of the surrounding tissue 3. After insertion of the device, surrounding tissue attempts to resume its previous position, collapsing around the individual coils 4 of the device and tending to herniate at points 20 through the spaces between the coils 4. The herniation points extending into the interior 6 of the device 2 engage the pellet 14 to help maintain it is position so that it does not migrate through either end or through the spaces between the coils 4.

It should be noted that the pellet may comprise or is known in the medical device or to comprise a pill or tablet like article formed from inert substances compressed together; the substances are normally absorbable in the body. The pellet may be formed with a radiopaque seed to provide radiographic visibility of the implant location. In a preferred embodiment the pellet may have a generally cylindrical shape having a diameter on the order of 0.060 inches and a thickness of 0.028 inches. In experiments it has proven desirable to have approximately 0.002 inches of clearance between the pellet and the inside diameter of the coils 4 in the larger coiled proximal region 10 (as well as the captured portion 28—after the proximal coils 10 have been crimped). Therefore, the preferable inside diameter of the coils 4 through a proximal region 10 would be on the order of 0.065 inches. It has also been found desirable to have the restraining coils of small diameter such as those at the distal portion 8 to be approximately 0.002 inches smaller in inside diameter than the diameter of the pellet. Therefore, the preferable inside diameter for distal coils 8 would be approximately 0.055 to 0.056 inches. Likewise, it is preferable to have spacing between adjacent coils 4 of the implant device 2 to be no more than approximately 0.026 inches. So that the pellet does not migrate through the space between the coils.

Alternatively, it is possible, and in some cases desirable to have a friction fit between the pellet and the inside diameter of the coils. So configured, there would be no clearance around an installed pellet and the implant device coils. The friction fit permits the pellet to be delivered into the device and retained without crimping the proximal coils behind the pellet to retain it, thereby potentially eliminating a delivery step. When a pellet is configured to have zero clearance with the inside diameter of the device, the pellet may be shaped to have a smaller profile distal end (leading edge) to be more easily insertable into the narrow opening of the device. An example of such a shape would be a cone shape pellet (not shown).

Figure 3A:
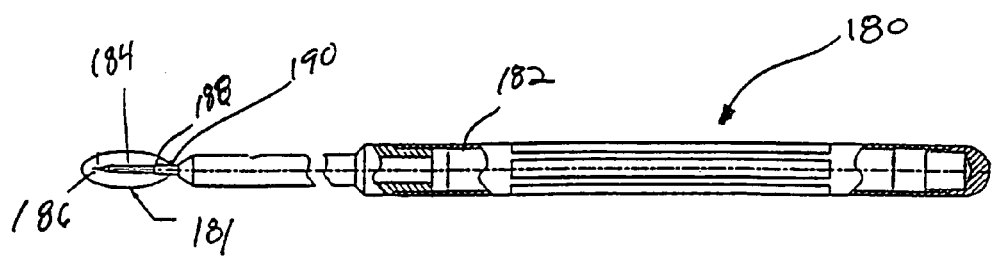
FIG. 3A. is a side view of an implant delivery device.
Figure 3B:
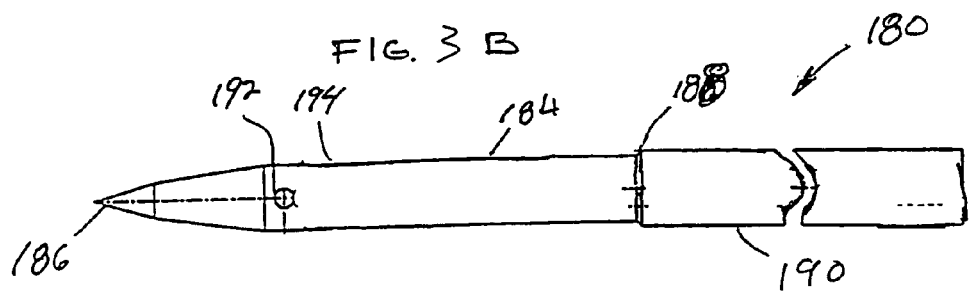
FIG. 3B. is a detail of the distal tip of the implant delivery device shown in FIG. 3A.
Figure 3C:
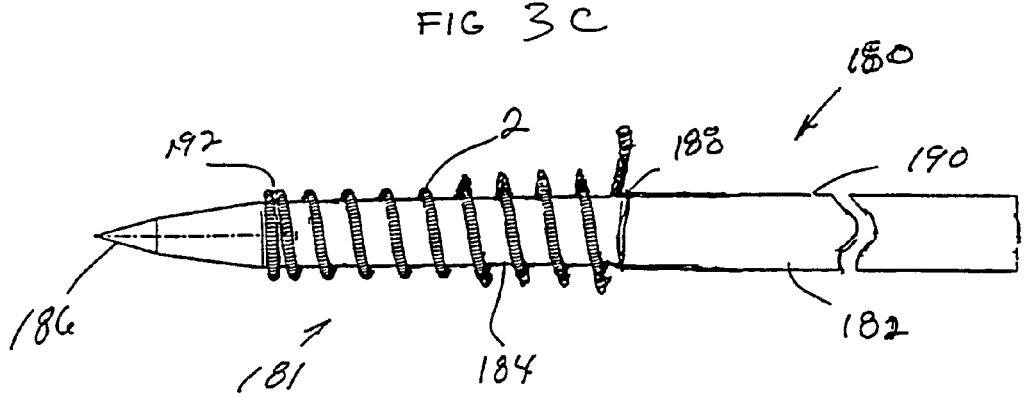
FIG. 3C. is a detail of the distal tip of an implant delivery device shown in FIG. 3A carrying an implant.

The implant devices 2 of the present invention may be delivered to their intended tissue location either percutaneously, with a catheter based system, transthoracically or surgically. FIGS. 3A–3C show an example of a surgical delivery device that may be used to deliver the implants into tissue such as that of the myocardium of the heart. The delivery device, shown in FIG. 3A, comprises an obturator 180 that includes a main shaft 182, by which it can be gripped and manipulated. The distal end 181 of the shaft 182 is shown in detail in FIG. 3B and includes a reduced diameter device support section 184 having a sharp distal tip 186 adapted to pierce tissue. The diameter of the shaft segment 184 is selected to fit closely within the interior 6 of the devices 2. The proximal end of the segment 184 terminates in a shoulder 188 formed at the junction of a proximally adjacent, slightly enlarged diameter portion 190 of the shaft. The distal end of the device support segment 184 may include a radially projecting pin 192 dimensioned to project and fit between adjacent turns of the coils 4. The pin 192 engages the coils in a thread-like fashion so that after the assembly has been inserted into the tissue, the obturator 180 can be removed simply by unscrewing the obturator to free it from the implanted coil. Alternatively, the obturator may be configured without the projecting pin 192 so that the device can be slipped on and off the obturator, without screwing. When the implant device 2 is mounted on the obturator 180, the proximal end of the device may bear against the shoulder 188, and the tail 16, depending on its configuration, may extend away from or along the segment 190 of the obturator.

In use, the intended tissue location is first accessed surgically, such as by a cut-down method. The obturator, with an implant device loaded on to segment 184, as shown in FIG. 3C, then may be advanced into the tissue to deliver the implant. The sharp tip pierces the tissue permitting the obturator and implant to be pushed inward into the tissue. In the example of delivery to the myocardium, the epicardial surface of the heart is accessed and penetrated by the obturator to deliver the implant. The pin 192 and/or shoulder 188 prevents proximal movement of the implant along segment 184 during delivery. Preferably, the distal end of the obturator is projected to, and slightly beyond, the endocardium to place the implant device. The obturator then may be unscrewed and separated from the implant device. If the obturator is configured without the pin 192, the obturator may be withdrawn directly from the device and the tissue. Simply applying light closure pressure to the epicardial puncture will cause the puncture hole to clot at the epicardium.

Figure 4:
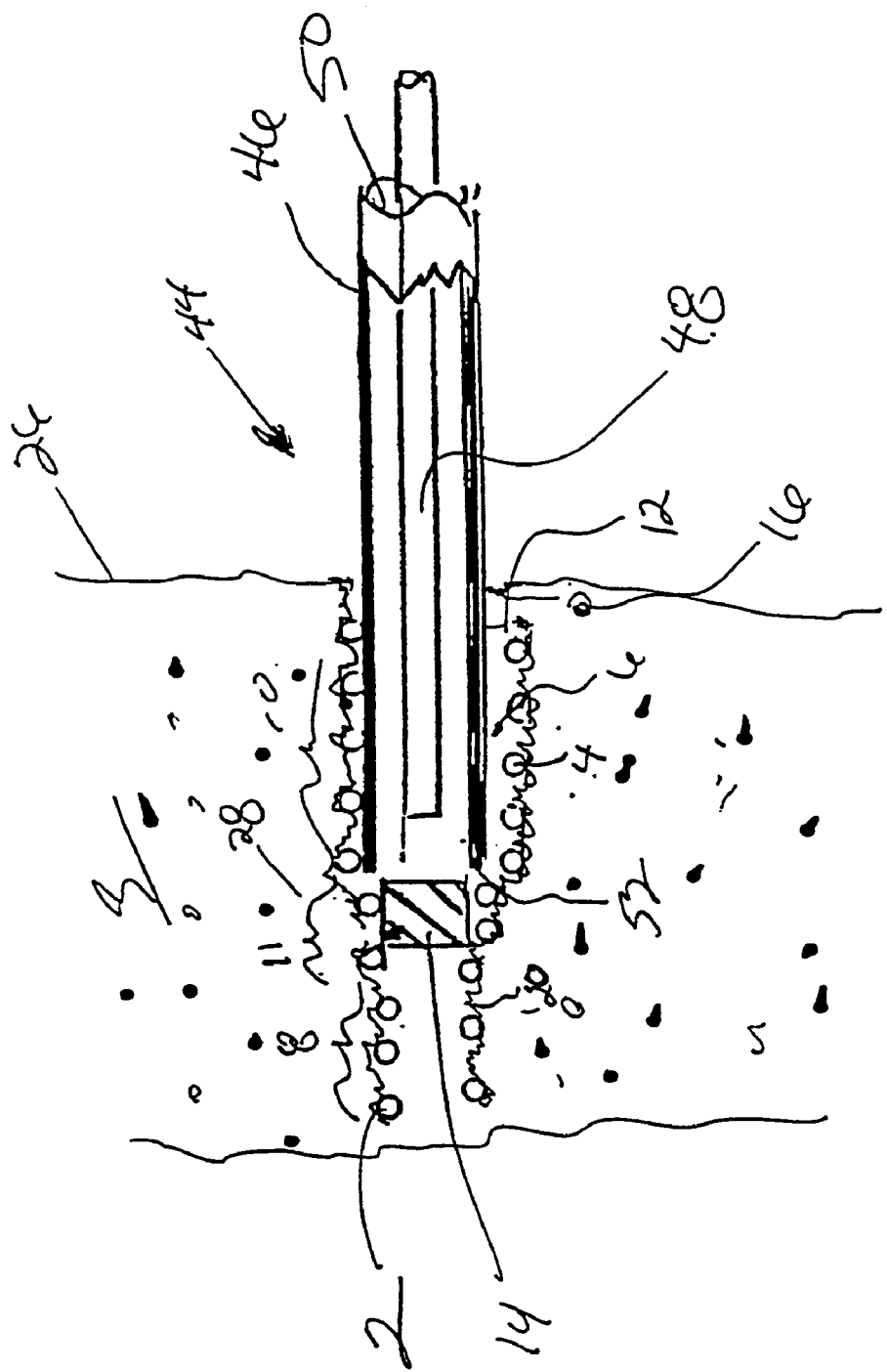
FIG. 4. is a partial sectional side view of an implant device and pellet delivery system.

FIG. 4 shows a partial sectional view of an embodiment of an agent delivery system 44. The delivery device 44 comprises a flexible tube 46 that is sized to fit within the interior of the implant device 2, specifically within the coils 4 of the proximal region 10. FIG. 4 shows a modified version of the implant device having, in an addition to the distal portion 8 and proximal portion 10, a mid portion 11 having coils 6 defining a diameter that is between the smaller diameter of the distal portion and the larger diameter of the proximal portion. It is this mid portion 11 that will become the capture portion 28 of the device where the pellet 14 will reside after it is installed into the implant. After the implant 2 has been delivered into the tissue 3 such as that of the myocardium of the heart, by the method and use of an obturator as described above, the flexible tube 46, loaded with the pellet 14, is inserted into the proximal end 10 of the device through proximal opening 12. A push rod 48 slidably received within the lumen 50 of the flexible tube 46 is advanced distally, pushing the pellet 14 out from the distal end 52 of the tube 46 and into the interior 6 of the implant device. After ejection of the pellet 14, the tube 46 and push rod 48 may be withdrawn proximally from the tissue 3 and device 2. The proximal portion 10 of the implant device is then crimped to a smaller diameter by means such as a sterilized forceps. At least one coil needs to be crimped to the reduced diameter discussed above sufficient to restrain the pellet 14. It is acceptable for the pellet to have some freedom of movement within the capture portion 28 of the device after it is implanted.

Figure 5:
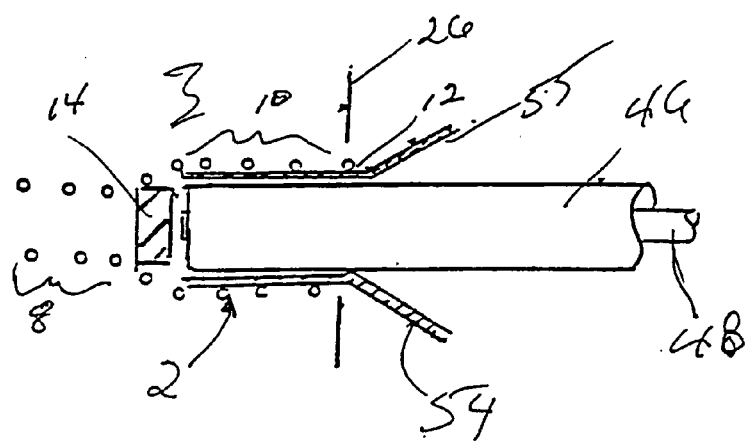
FIG. 5. is a partial sectional side view of a pellet and implant device delivery system and alignment tool.

FIG. 5 shows a partial sectional side view of the agent delivery system and an alignment tool 54. The agent delivery system shown in FIG. 5 operates identically to that described in connection with FIG. 4 but makes use of a funnel shaped alignment tool 54 to help guide the flexible tube 46 into the proximal opening of the implant 2 after it has been placed into tissue 3. In situations where the implant has been delivered into muscle tissue that is highly dynamic such as the myocardium of the heart, it may be difficult to align the distal end 52 of the flexible tube with the implanted device 2 due to movement of the device in the dynamic tissue. The device may be inserted into the tissue over the obturator as described above while having in place the alignment tool 54 so that when the obturator is removed the surface of the tissue 26, such as the epicardium in the case of the myocardial tissue, will be held back so that the proximal opening 12 of the device is open and ready to receive the pellet 14. The alignment tool may be formed from any rigid polymer material and is dimensioned at its distal end 53 to fit snugly within the inside diameter of the proximal portion 10 of the implant device 2. The proximal end 55 defines a funnel shape, opening to a diameter that is significantly greater than the agent delivery tube 46 to facilitate reception of the tube into the alignment tool.

Figure 6:
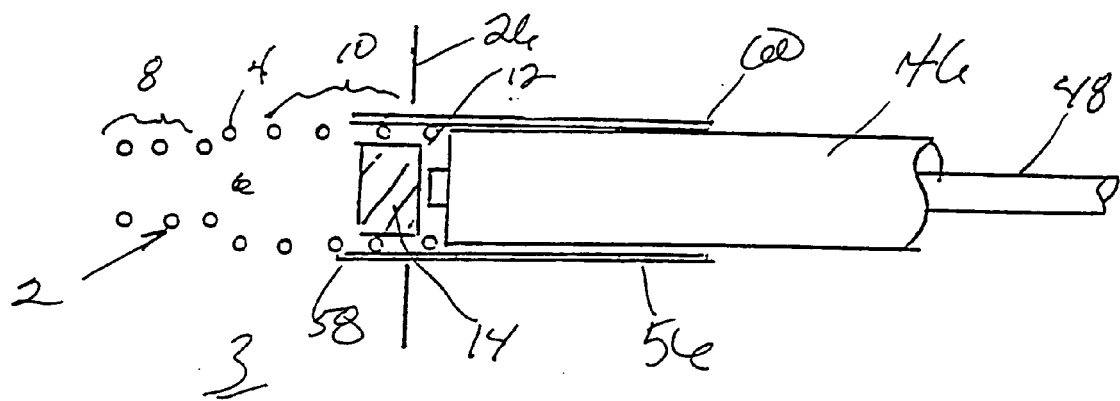
FIG. 6. is a Partial sectional side view of a pellet and implant device delivery system and alignment tool.

FIG. 6 shows another alignment tool 56 to help navigate the flexible tube 46 into the proximal opening 12 of the implant device so that a pellet 14 may be delivered. The outer fitting alignment tool 56 may also be formed from a rigid polymer and may be applied to the implant device 2 prior to delivery into the tissue 3. The outer alignment tool 56 is dimensioned to have a distal end 58 that is slightly larger than the outside diameter of the proximal portion 10 of the implant 2. This is in contrast to the distal end 53 of the inner alignment tool discussed above, which is dimensioned to fit within the coils of the proximal portion 10 of the implant device. Additionally, the proximal end 60 of the present alignment tool is the same diameter as the distal end 58 but still sufficiently large to receive the distal end 52 of the flexible tube 46. The proximal end is also contrasted with the proximal opening 55 of the above described alignment tool which has a larger flared open diameter to help receive the flexible tube 46.

FIG. 7 shows another partial sectional side view of the pellet delivery tube 46 delivering a pellet 14 into the implant device 2. The flexible tube 46 uses an optional backstop 62 to control the depth to which the tube 46 is inserted into the proximal portion 10 of the implant device 2. It is helpful to control the depth which the flexible tube is inserted into the implant 2 so that the implant is not pushed out of position in a distal direction by an aggressive insertion. The backstop 62 may comprise a flange formed from a rigid polymer material fixed to the pellet delivery tube 46 by means such as adhesive. The backstop can be positioned on the delivery tube an appropriate distance such that the distal end 52 of the pellet delivery tube is maintained the proper distance within the implant.

Additionally, FIG. 7 shows one example of a pellet movement regulating mechanism, which comprises a slit 64 along the length of the flexible tube 46. The slit 64 permits the pellet delivery tube 46 to have a variable diameter, which serves to maintain a tight fit on a pellet that is being advanced through the tube so that it does not slide freely through the tube out of control of the operator. FIG. 8A shows an end view of the flexible tube 46 when a pellet 14 is present in the tube. FIG. 8A shows larger diameter D1 of the flexible tube because of the presence of the pellet 14 in the lumen 50 of the tube 46. After the pellet has been ejected from the tube, it resiliently returns to a smaller diameter configuration shown as D2 in FIG. 8B. The slit 64 permits the change in diameter of the tube. The natural resilience of the polymer material of the tube causes the tube to be biased to the diameter D2. The inherent bias causes a force to be applied to any pellet 14 in the lumen 50 because the pellet forces the tube to increase in diameter greater than D2. Therefore, the movement of the pellet as restrained by frictional contact with the inside surface of the lumen 50.

FIG. 9 shows an alternate mechanism for restraining the movement of a pellet 14 within flexible tube 46. FIG. 9 shows a flexible tube 46 having resiliently inwardly projecting fingers 66 around the circumference of the distal end 52 of the flexible tube. The inwardly projecting fingers 66 serve to catch a pellet and restrain it from exiting the distal end 52 of the tube until a sufficient force is applied by the push rod 48 to overcome the natural resiliency of the fingers 66. Alternatively, the pellet may be restrained by other means attached to the push rod 48, such as a small plunger mechanism (not shown). Alternatively, the pellet may be configured to have a hole or other shape graspable by an attachment to the push rod 48 in order to regulate distal movement of the pellet.

FIG. 10 shows a partial sectional side view of an alternative agent delivery system 70. A short multi-lumen tube or catheter 72 permits the implant and pellet delivery systems to be combined in one device to facilitate pellet delivery after implant delivery. The multi-lumen tube offers an implant lumen 74 and a pellet lumen 76 for independent manipulation of the implant and pellet delivery devices through a single instrument that maintains communication with the tissue implant site throughout the procedure. The multi-lumen tube 72 has a tissue positioning mechanism 84 at its distal end 79 which serves to locate the distal end 79 of the tube throughout the implant and pellet delivery procedure. The positioning system may comprise a circumferential ring 83 extending around the distal end 79 of the tube and having distally projecting barbs 86 that extend distally from the distal end 79 of the tube 72. When the distal end 79 of the tube is brought flush to the tissue surface 26, the barbs protrude slightly into the tissue 3 maintaining the catheter at the intended location as long at least a slight distal force is maintained on the multi-lumen tube 72.

Implant device 2 is shown being delivered over a modified obturator device 78 having shaft 80 which holds the implant during penetration of the obturator 78 into tissue 3. The pellet lumen 76 permits independent movement of pellet delivery tube 46 and its respective push rod 48. The pellet lumen 76 joins the main implant lumen 74 just prior to the distal end of the multi-lumen tube 72. This arrangement facilitates the delivery process as will be described below.

FIGS. 11A through 11D show the sequence of delivery steps utilizing the multi-lumen catheter 72 discussed above in connection with FIG. 10. In FIG. 11A, the implant device 2 is inserted over obturator device 78 and obturator shaft 80. The implant device is inserted into the tissue by distal force and rotational motion of the obturator to screw the implant into the tissue 3. FIG. 11B the implant device 2 is shown inserted in tissue 3 and the obturator 78 has penetrated the tissue to create a cavity 18 in the tissue into which the pellet may reside. FIG. 11C shows the obturator 78 and shaft 80 being withdrawn proximally through the implant lumen 74 of the multi-lumen catheter/tube 72. Positioning mechanism 84 maintains the distal end 79 of the tube in position. The pellet delivery tube 46 is advanced distally through pellet lumen 76 which leads to main implant lumen 74 and the distal end 79 of the tube, which is still in contact with the tissue surface 26. Once the pellet delivery tube has reached the distal end of the multi-lumen tube 72, the push rod 48 may be advanced distally to eject the pellet 14 into the cavity 18 created within the interior of the device by the obturator 78. In FIG. 11D both the pellet delivery tube 46 and implant delivery system obturator 78 and shaft 80 have been withdrawn proximally into their respective lumens and the implant device 2 and pellet 14 are left remaining in tissue 3.

FIGS. 12A through 12E show an alternate agent implant system wherein the pellet 14 and implant device 2 are delivered simultaneously into tissue 2. FIG. 12A shows an obturator 90 of conventional configuration forming a cavity 18 into tissue 3 in preparation for simultaneous delivery of the implant 2 and pellet 14. FIG. 12B shows the open cavity 18 created in the tissue by the piercing action of obturator 90. FIG. 12C shows the insertion device 92 holding both the implant 2 and pellet 14 within the interior 6 of the implant as it approaches the cavity 18 formed in the tissue 3. By pre-forming the cavity 18 with obturator 90, the insertion tool 92 need not have a obturator tip extending through the length of the implant device 2, which would preclude the presence of the pellet 14 in the interior 6 of the implant. The insertion tool 92 grasps the implant device 2 at its tail 16 which is squeezed in notch 94 formed in the sidewall of the tubular insertion device 92. In the figures an alternate embodiment of the tail 16 having a broad loop coil is shown. In FIG. 12D the insertion tool 92 continues to deliver the implant device 2 into the cavity 18 formed in the tissue 3 by rotating the coiled implant into position. The pellet 14 is captured in the interior 6 of the coil by the presence of the insertion tool and the smaller diameter distal coils. Specifically, the distal coils 8 of implant 2 have a smaller diameter which does not permit passage of the pellet 14. Proximal movement of the pellet 14 is prevented by the presence of the insertion tool 92. In FIG. 12E, the implant device and pellet are shown delivered into the tissue 3 and the insertion tool 92 is withdrawn proximally so that the distal end 98 is withdrawn from the interior 6 of the implant device. The pellet and device of the present embodiment are configured to have a friction fit so that crimping of a device coil proximal to the pellet is not required.

From the foregoing it should be appreciated that the invention provides an agent delivery system for delivering an agent carrying pellet and implant device in combination. The invention is particularly advantageous in promoting angiogenesis within an ischemic tissue such as myocardial tissue of the heart. The delivery system is simple to use and requires a minimum of steps to practice.

It should be understood, however, that the foregoing description of the invention is intended merely to be illustrative thereof and that other modifications, embodiments and equivalents may be apparent to those skilled in the art without departing from its spirit. Having thus described the invention what we desire to claim and secure by Letters Patent is:

The invention claimed is:

1. A system for delivering an agent to tissue, comprising:
a pellet containing a therapeutic agent;
a flexible body implantable in tissue, comprising a coil defining a hollow interior configured to receive and retain the pellet within the interior after the body has been implanted within tissue, the body having at least one opening sized to permit bodily fluid to enter the interior and come in contact with the pellet.

2. An agent delivery system as defined in claim 1 wherein the implantable body comprises a helical spring having individual coils which define an inside diameter suitable for retaining the pellet in position within the device and the coils being spaced a distance which permits bodily fluids to flow into the interior of the device yet are small enough to prevent passage of the pellet from the interior of the device.

3. An agent delivery system as defined in claim 2 wherein the body has proximal and distal portions and coils along the proximal portion define a second inside diameter that does not accept the pellet.

4. An agent delivery system as defined in claim 2 wherein the coils at the distal portion of the body further define a diameter that does not accept the pellet.

5. An agent delivery system comprising:
a pellet containing a therapeutic agent;
a flexible and implantable body defining an interior sized to accept the pellet and having proximal and distal ends, wherein the proximal end is sized to accept the pellet and retain the pellet after the body has been implanted within tissue, the body further having at least one opening sized to permit bodily fluid to enter the interior but sized to prevent the pellet from exiting the interior;
an implant delivery device;
a pellet delivery tube engagable with the proximal end of the body.

6. An agent delivery system as defined in claim 5 further comprising an alignment tool engagable with the interior of the implant body.

7. An agent delivery system as defined in claim 5 further comprising an alignment tool engagable with an outside surface of the implant device and pellet delivery tube.

8. An agent delivery system as defined in claim 5 wherein the pellet delivery tube further comprises a pellet advancement mechanism and a pellet restraint mechanism.

9. An agent delivery system comprising:
a pellet containing a therapeutic agent;
a flexible, implantable implant device;

a multi-lumen delivery tube having an implant delivery lumen and a pellet delivery lumen and having a distal end with a catheter positioning device engagable with tissue;

an implant delivery device comprising:

an obturator capable of piercing tissue in a shaft joined to the obturator for controlling axial movement of the delivery device through the multi-lumen catheter;

a pellet delivery tube sized to slidably receive a pellet and being slidable within the pellet delivery lumen of the multi-lumen catheter, the implant device delivery device and pellet delivery tube being independently controllable through the multi-lumen delivery catheter.

10. An agent delivery system comprising:

a pellet containing a therapeutic agent;

a flexible, implantable body having an interior configured to receive the pellet and retain it after the implantable body has been placed in tissue;

an obturator configured to pierce tissue;

an insertion device configured to retain the pellet within the interior of the implantable body for simultaneous delivery into an intended tissue location.

11. A method for delivering an agent comprising:

providing a pellet containing a therapeutic agent;

providing a flexible implantable body having an interior configured to receive and retain the pellet;

providing an obturator capable of piercing tissue;

providing a pellet delivery tube advancing the obturator into the tissue to create a channel;

advancing the implantable body into the channel;

advancing the pellet delivery tube to the proximal end of the body and inserting the pellet into the interior of the body;

closing the proximal end of the body to retain the pellet within the interior.

* * * * *